United States Patent
Yamasita et al.

[11] 4,042,295
[45] Aug. 16, 1977

[54] RETROFOCUS-TYPE OBJECTIVE FOR ENDOSCOPES

[75] Inventors: Nobuo Yamasita, Tama; Toshihiro Imai, Hachiouji, both of Japan

[73] Assignee: Olympus Optical Co., Inc., Japan

[21] Appl. No.: 622,115

[22] Filed: Oct. 14, 1975

[30] Foreign Application Priority Data

Oct. 15, 1974   Japan .................................. 49-117749

[51] Int. Cl.² ............................................. G02B 13/04
[52] U.S. Cl. ...................................... 350/202; 350/225
[58] Field of Search ............... 350/230, 255, 186, 225, 350/202

[56] References Cited

U.S. PATENT DOCUMENTS

| 2,893,717 | 7/1959 | Simmons | 350/255 |
| 3,576,358 | 4/1971 | Hayamizu et al. | 350/175 TS |

FOREIGN PATENT DOCUMENTS

| 455,426 | 1949 | Italy | 350/230 |

*Primary Examiner*—John K. Corbin
*Assistant Examiner*—Conrad Clark
*Attorney, Agent, or Firm*—Cushman, Darby & Cushman

[57] ABSTRACT

A retrofocus-type objective for endoscopes comprising a front diverging lens group and rear converging lens group and arranged to be focused by keeping the front diverging lens group fixed and moving the rear converging lens group toward the front diverging lens group.

2 Claims, 4 Drawing Figures

RETROFOCUS-TYPE OBJECTIVE FOR ENDOSCOPES

BACKGROUND OF THE INVENTION a. Field of the invention:

The present invention relates to an objective for endoscopes and, more particularly, to a retrofocus-type objective for endoscopes.

b. Description of the prior art:

Known objectives for endoscopes are generally focused by advancing the lens system as a whole. Besides, a retrofocus-type lens system is known as a lens system by which the image plane can be made flat over a wide area. For the retrofocus-type lens system, however, the aperture stop is arranged in the inside of the lens system. Consequently, the position of the entrance pupil comes off the front lens surface of the lens system and, therefore, the front lens diameter becomes large.

Besides, for endoscopes, a cover glass for waterproof purpose is provided in front of the objective for endoscopes. When, therefore, the objective for endoscopes is to be focused by advancing the lens system as a whole in case of an endoscope employing a retrofocus-type objective with a large front lens diameter, the airspace between the cover glass and lens system is to be varied and, consequently, the cover glass diameter becomes very large. It is, however, not desirable to make the cover glass diameter large because pain of the patient will increase.

SUMMARY OF THE INVENTION

It is, therefore, a primary object of the present invention to provide an objective for endoscopes of a retrofocus-type lens configuration comprising a front diverging lens group and rear converging lens group, said front diverging lens group consisting of a concave lens which is arranged to serve also as a cover glass for waterproof purpose and is fixed, said rear converging lens group being arranged movable, said objective for endoscopes being arranged to be focused by moving said rear converging lens group.

FIG. 1 shows the basic configuration of the retrofocus-type lens system comprising a front diverging lens group 1 and rear converging lens group 2. In this lens system, the formula (1) below is true when reference symbol $f$ represents the focal length of the lens system as a whole, the total focal length of the front diverging lens group 1 is $f_F = -mf$, the total focal length of the rear converging lens group 2 is $f_B = nf$, the advancing length of the rear converging lens group is $\Delta$. $f$, the distance from the front focal point $F_1$ of the front diverging lens group to the object is $x_1 = -kf$, reference symbol $\beta$ represents magnification of the rear converging lens group and reference symbol $x_1'$ represents the image position of the front diverging lens group 1.

$$x_1' = \frac{(f_F)^2}{x_1} = f_B\left(\beta + \frac{1}{\beta} - 2\right) \tag{1}$$

From the above, $$\frac{m^2}{K} = n\left(\beta + \frac{1}{\beta} - 2\right) \tag{2}$$

As $f = f_F \beta$, it becomes $$m\beta = 1 \tag{3}$$

From the above formulas (2) and (3), it becomes $$K = \frac{m^3}{n(m-1)^2} \tag{4}$$

When the formula (4) is differentiated, it becomes $$\frac{\delta K}{\delta m} = \frac{m^2(m-3)}{n(m-1)^3} \tag{5}$$

$$\frac{\delta K}{\delta m} = 0, m = 3.$$

Therefore, the value of K becomes minimum at the time of $m = 3$ and, consequently, the distance from the front lens surface to the object on which the lens system can be focused becomes the shortest at the time of $m = 3$.

Besides, the advancing length of the rear lens group is expressed by $$\Delta \cdot f = f_B\left(\frac{1}{\beta} - 1\right) \tag{6}$$

and, the following formula (7) is led from the above formula (6).

$$\frac{\Delta}{n} = m - 1 \tag{7}$$

FIG. 2 shows a graph illustrating the relation between $K/K_{M=3}$ and $m$ and relation between $\Delta/n$ and $m$ based on the above formulas (4) and (7). From FIG. 2, the following fact is evident. That is, as the range of distance from the endoscope objective to the object for focusing the objective on an object at a short distance and as the range near the value of $m = 3$ at which it is possible to focus the objective on the object at the shortest distance, the range from $K/K_{m=3} = 1$ to $K/K_{m=3} \approx 3.5$ is preferable. Therefore, the preferable range of $m$ is $1.3 < m < 20$.

On the other hand, it is desirable that the advancing length of the rear lens group is smaller. When this is taken into consideration, it is desirable that the value of $m$ is about $m < 4$ and, consequently, the most preferable range of $m$ is $1.3 < m < 4$.

Besides, to focus the lens system on an object at as far as possible short distance, the value of K is to be made smaller. For this purpose, it is desirable to make the value of $n$ as large as possible as it is evident from the formula (4). If, however, the value of $n$ is made large, the advancing length of the rear lens group 2 becomes large and, therefore, the value of $n$ should be within a certain limit. By taking the above into consideration, it is desirable to make the range of value of $n$ as $1.4 < n < 3.5$. Here, the upper limit $n < 3.5$ is the condition required for focusing the lens system on an object at a short distance and the lower limit $1.4 < n$ is the condition for preventing the advancing length of the rear lens group from becoming large.

DETAILED DESCRIPTION OF THE PREFERRED EMBODIMENTS

Preferred embodiments of the retrofocus-type objective for endoscopes according to the present invention explained in the above are as shown below.

Figure 1:
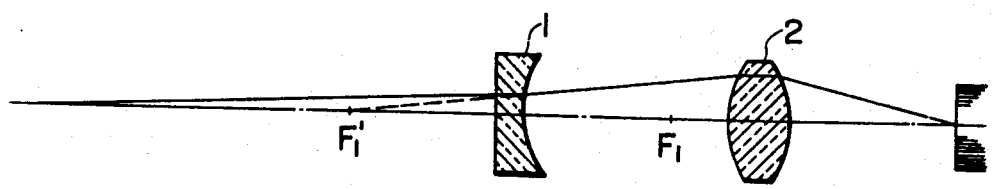
FIG. 1 shows a sectional view for explaining the principle of the objective for endoscopes according to the present invention.
Figure 2:
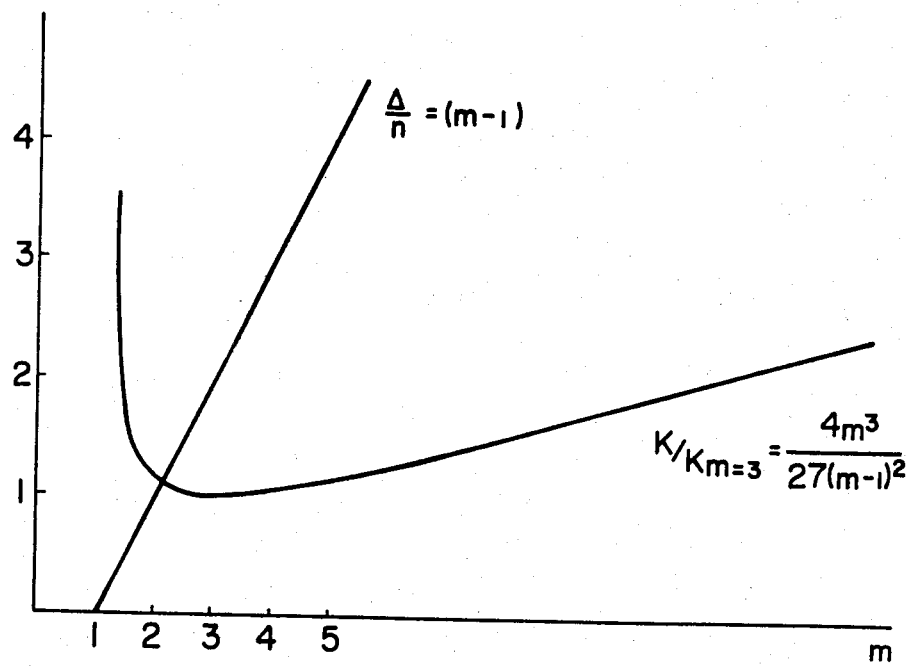
FIG. 2 shows a graph illustrating the relation of the advancing amount of the rear lens group, focal length of the front lens group and focal length of the rear lens group and the relation of the distance from the lens system to the object and the focal length of the front lens group.
Figure 3:
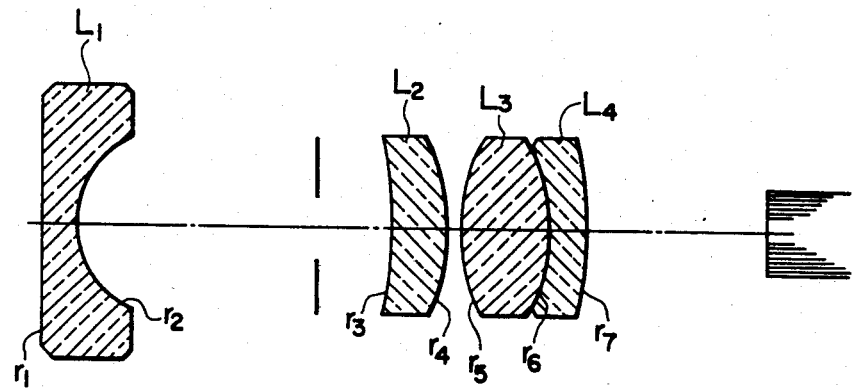
FIG. 3 and 4 respectively show sectional views of respective embodiments of the present invention.

A first embodiment of the present invention is a lens system of the lens configuration as shown in FIG. 3 comprising a front diverging lens group and rear converging lens group, said front diverging lens group comprising a first lens component which is a negative lens $L_1$, said rear converging lens group comprising a second lens component which is a positive lens $L_2$ and a third lens component which is a cemented doublet lens consisting of a positive lens $L_3$ and a negative lens $L_4$. Said first embodiment has the following numerical values.

```
r_1 = ∞
     d_1 = 0.6        n_1 = 1.51633     ν_1 = 64.1
r_2 = 1.685
     d_2 = 5.36
r_3 = −7.54
     d_3 = 1.0        n_2 = 1.69680     ν_2 = 55.7
r_4 = −3.2
     d_4 = 0.2
r_5 = 3.127
     d_5 = 1.6        n_3 = 1.62041     ν_3 = 60.3
r_6 = −2.483
     d_6 = 0.55       n_4 = 1.84666     ν_4 = 23.9
r_7 = −8.619
     f = 1.465    , f_B = 2.961   , f_F = −3.263
     F_NO = 3.5   , 2ω = 88°40'
     m = 2.227    , n = 2.021
```

The advancing length of the rear lens group for focusing of the first embodiment is as shown below.

When distance to object is ∞, $t_1 = 1.23$, $t_2 = 3.1$
When distance to object is 15 mm, $t_1 = 1.027$, $t_2 = 3.3$
When distance to object is 5 mm, $t_1 = 0.729$, $t_2 = 3.6$ In the above, reference symbol $t_1$ represents the distance from the stop to the surface on the object side of the second lens component $L_2$, and reference symbol $t_2$ represents the distance from the surface of the image side of the lens system to the image guide.

Figure 4:
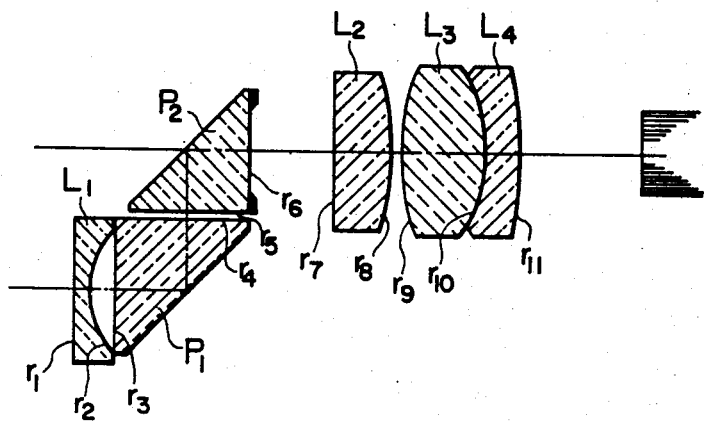

A second embodiment of the present invention is a lens system of the lens configuration as shown in FIG. 4 and comprises two prisms $P_1$ and $P_2$ arranged between the front diverging lens group and rear converging lens group. Said second embodiment has the following numerical values.

```
r_1 = ∞
     d_1 = 0.3        n_1 = 1.51633     ν_1 = 64.1
r_2 = 1.392
     d_2 = 0.4
r_3 = ∞
     d_3 = 2.4        n_2 = 1.80610     ν_2 = 40.8
r_4 = ∞
     d_4 = 0.1
```

-continued
```
r_5 = ∞
     d_5 = 2.2        n_3 = 1.80610     ν_3 = 40.8
r_6 = ∞
     d_6 = t_1
r_7 = ∞
     d_7 = 1.0        n_4 = 1.69680     ν_4 = 55.7
r_8 = −4.09
     d_8 = 0.2
r_9 = 3.902
     d_9 = 1.5        n_5 = 1.62041     ν_5 = 60.3
r_10 = −2.19
     d_10 = 0.5       n_6 = 1.78472     ν_6 = 25.7
r_11 = −6.541
     f = 1.506    , f_B = 2.901   , f_F = −2.696
     F_NO = 2.5   , 2ω = 55°23'
     m = 1.790    , n = 1.926
```

The advancing length of the rear lens group for focusing of the second embodiment is as shown below.

When distance to object is ∞, $t_1 = 1.424$, $t_2 = 3.331$
When distance to object is 15 mm, $t_1 = 1.2$, $t_2 = 3.555$
When distance to object is 7 mm, $t_1 = 0.912$, $t_2 = 3.843$
When distance to object is 5 mm, $t_1 = 0.62$, $t_2 = 4.135$ In the above, reference symbol $t_1$ represents the distance from the stop to the surface on the object side of the second lens component $L_2$, and reference symbol $t_2$ represents the distance from the surface on the image side of the lens system to the image guide.

As explained in the above, the retrofocus-type objective for endoscopes according to the present invention is arranged to be focused by moving the rear converging lens group toward the front diverging lens group. Therefore, the front lens of the objective is to be kept fixed. Consequently, by making the front lens serving also as the cover glass, it is possible to make the distal end of endoscopes small by employing a retrofocus-type objective.

We claim:

1. A retrofocus-type objective for endoscopes comprising a front diverging lens group and rear converging lens group, said front diverging lens group comprising a negative lens, said rear converging lens group comprising a positive lens and a positive cemented doublet lens, said retrofocus-type objective for endoscopes being arranged to be focused on an object to be observed by keeping said front diverging lens group fixed and by moving said rear converging lens groups toward said front diverging lens group when the distance from said objective to the object to be observed becomes shorter, said retrofocus-type objective for endoscopes having numerical values as given below:

```
r_1 = ∞
     d_1 = 0.6        n_1 = 1.51633     ν_1 = 64.1
r_2 = 1.685
     d_2 = 5.36
r_3 = −7.54
     d_3 = 1.0        n_2 = 1.69680     ν_2 = 55.7
r_4 = −3.2
     d_4 = 0.2
r_5 = 3.127
     d_5 = 1.6        n_3 = 1.62041     ν_3 = 60.3
r_6 = −2.483
     d_6 = 0.55       n_4 = 1.84666     ν_4 = 23.9
r_7 = −8.619
     f = 1.465    , f_B = 2.961   , f_F = −3.263
     F_NO = 3.5   , 2ω = 88°40'
     m = 2.227    , n = 2.021
``` wherein reference symbols $r_1$ through $r_7$ respectively represent radii of curvature of respective surfaces of respective lenses, reference symbols $d_1$ through $d_6$ respectively represent thicknesses of respective lenses and airspaces between respective lenses, reference symbols $n_1$ through $n_4$ respectively represent refractive indices of respective lenses, reference symbols $\nu_1$ through $\nu_4$ respectively represent Abbe's numbers of respective lenses, reference symbol $f$ represents the focal length of the lens system as a whole, reference symbol $f_F$ represents the total focal length of the front lens group and reference symbol $f_B$ represents the total focal length of the rear lens group.

2. A retrofocus-type objective for endoscopes comprising a front diverging lens group, two prisms and rear converging lens group, said front diverging lens group comprising a negative lens, said rear converging lens group comprising a positive lens and a positive cemented doublet lens, said retrofocus-type objective for endoscopes being arranged to be focused on an object to be observed by keeping said front diverging lens group fixed and by moving said rear converging lens group toward said front diverging lens group when the distance from said objective to the object to be observed becomes shorter, said retrofocus-type objective for endoscopes having numerical values as given below:

$r_1 = \infty$
　　$d_1 = 0.3$　　$n_1 = 1.51633$　　$\nu_1 = 64.1$
$r_2 = 1.392$
　　$d_2 = 0.4$ -continued $r_3 = \infty$
　　$d_3 = 2.4$　　$n_2 = 1.80610$　　$\nu_2 = 40.8$
$r_4 = \infty$
　　$d_4 = 0.1$
$r_5 = \infty$
　　$d_5 = 2.2$　　$n_3 = 1.80610$　　$\nu_3 = 40.8$
$r_6 = \infty$
　　$d_6 = t_1$
$r_7 = \infty$
　　$d_7 = 1.0$　　$n_4 = 1.69680$　　$\nu_4 = 55.7$
$r_8 = -4.09$
　　$d_8 = 0.2$
$r_9 = 3.902$
　　$d_9 = 1.5$　　$n_5 = 1.62041$　　$\nu_5 = 60.3$
$r_{10} = -2.19$
　　$d_{10} = 0.5$　　$n_6 = 1.78472$　　$\nu_6 = 25.7$
$r_{11} = -6.541$
　　$f = 1.506$　,　$f_B = 2.901$　,　$f_F = -2.696$
　　$F_{NO} = 2.5$　,　$2\omega = 55°23'$
　　$m = 1.790$　,　$n = 1.926$ wherein reference symbols $r_1$ through $r_{11}$ respectively represent radii of curvature of respective surfaces of respective lenses, reference symbols $d_1$ through $d_{10}$ respectively represent thicknesses of respective lenses and airspaces between respective lenses, reference symbols $n_1$ through $n_6$ respectively represent refractive indices of respective lenses, reference symbols $\nu_1$ through $\nu_6$ respectively represent Abbe's numbers of respective lenses, reference symbol $f$ represents the focal length of the lens system as a whole, reference symbol $f_F$ represents the total focal length of the front lens group and reference symbol $f_B$ represents the total focal length of the rear lens group.

* * * * *